United States Patent [19]

Ashley et al.

[11] 4,309,112

[45] Jan. 5, 1982

[54] RATE MEASUREMENT ANALYZER

[75] Inventors: Holvor W. Ashley, Burlingame, Calif.; Vincent H. Li, Maryland Heights, Mo.

[73] Assignee: Sherwood Medical Industries Inc., St. Louis, Mo.

[21] Appl. No.: 178,850

[22] Filed: Aug. 18, 1980

Related U.S. Application Data

[63] Continuation of Ser. No. 39,150, May 15, 1979, abandoned.

[51] Int. Cl.³ .............................................. G01N 21/01

[52] U.S. Cl. .................................... 356/436; 250/565; 422/68

[58] Field of Search .................... 250/565; 356/39–42, 356/436, 223, 442, 306, 409, 414; 23/230 B; 422/67, 68

[56] References Cited

U.S. PATENT DOCUMENTS

| | | | |
|---|---|---|---|
| 3,542,515 | 11/1970 | Scott | 23/230 |
| 3,565,535 | 2/1971 | Monell | 356/432 |
| 3,633,012 | 1/1972 | Wilhelmson et al. | 356/432 X |
| 3,634,868 | 1/1972 | Pelavin et al. | 356/39 X |
| 3,703,336 | 11/1972 | Rosse et al. | 356/39 |
| 3,748,044 | 7/1973 | Liston | 356/432 X |
| 3,952,206 | 4/1976 | Liedholz | 250/565 |
| 3,989,382 | 11/1976 | Kent et al. | 356/39 |
| 4,035,087 | 7/1977 | Mori et al. | 250/565 X |
| 4,061,469 | 12/1977 | DuBose | 356/39 X |

*Primary Examiner*—John K. Corbin
*Assistant Examiner*—Bruce Y. Arnold
*Attorney, Agent, or Firm*—Wegner, Stellman, McCord, Wood & Dalton

[57] ABSTRACT

A method and apparatus for the detection of the magnitude of selected chemical substances in a biological fluid by fixed rate analysis. Photometric analysis is performed sequentially upon a standard solution and then upon an unknown sample to determine the rate reaction in each. The method and apparatus minimize or eliminate error in equipment drift and calibration. The rate reaction is manually initiated in a standard solution carrying a known amount of a chemical substance. The standard is then placed into a photodetector circuit to produce a voltage representing optical density which increases at a constant but unknown rate during the reaction. The time required for the voltage to change from a base-line level to a selected and pre-set value is then measured and stored as a calibration reference time. Then, the rate reaction in the sample carrying an unknown amount of the chemical substance is initiated and the standard is replaced by the sample in the same photodetector circuit to produce a voltage representing optical density of the unknown sample. The voltage representing the optical density of the unknown sample increases at a constant but unknown rate and the rate is proportional to the amount of chemical substance in the sample. The voltage level at the end of the calibration reference time represents the change in the optical density of the unknown sample which, in turn, indicates the amount of chemical substance in the sample with respect to the standard sample. The voltage level is then provided to a display which indicates the amount of the chemical substance in the sample.

13 Claims, 5 Drawing Figures

.082
CW
20K
20K
6
1558
7
10K
5
32
84
6PF
30PF
20M
5
6
MM5369
8
+15V
106
1
2
+5V
4049
7
6
8
114
.033
22K
360K
10/25V
2
555
6
7
3
1
4
8
42
+5V
+5V
12
14
.1
4011
11
13
116
82
80
5
4049
4
108
48
11
9
D
4013
S
8
12
Q
R
10
13
110
78
76
+5V
10K
22K
6
7
2
555
3
.033
1
4
8
118
+5V
74
124
122
120
4081
4049
4011
72
4081
126
+5V
70
44
14040
16
+5V
10
11
8
68
52
52
52
14516
14516
14516
128
4049
9
10
66
64
62
60
+5
+15V
30
NO
.01
755N
R
24
41
NC
2
3
5
G
28
C-1825-25
.01
-15V

1558
LF 398
4013
4011
4081
4049
CALIBRATE
TEST
IN914
IN4733
+5V
+15V
-15V

+15V
1K
10K
10K
CW
+5V
.1
14433
MPS A14
2.2K
172
170
168
160K
470K
160
104
102
100
98
96
94
92
76
88
86
4081
162
14511
164
68
166
MAN 74A
40
150
+5V

RATE MEASUREMENT ANALYZER

This is a continuation of application Ser. No. 39,150 filed May 15, 1979, now abandoned.

BACKGROUND OF THE INVENTION

The invention relates to a photometric measuring system and technique and, more particularly, to a system and technique for measuring amounts of chemical substances in biological fluids by using fixed time rate reactions.

Photometric analysis is widely used to determine the concentration of a chemical substance in fluids, such as biological fluids. Generally, the instruments operate on the principle that the absorption of light by the solution is directly proportional to the concentration of the solute in the solution, and that the absorption of light is independent of the intensity of the light passed through the fluid containing the solute. When biochemical substances possess characteristics which follow these two principles, photometric analysis of fluid samples having selected known concentrations of chemical substances can be employed to calibrate instruments for subsequent measurements of selected unknown sample concentrations, or to develop calibration curves for converting photometric readings directly into substance concentrations. The instrumentation that implements these principles has been severely limited because of the requirement for accurate operator calibration and accounting for variations in electrical components, the transmissibility of the reagents and other factors which affect the accuracy of the measurements.

When photometric measurements are used to produce standard curves for converting photometric readings directly into substance concentrations, readings are first taken at a variety of known concentrations. The readings are corrected by known techniques to compensate for changes caused by the disparity in the transmissibility of chemical reagents and are then plotted on graph paper at points representing the particular concentrations. Lines drawn through the majority of the points are used to determine the concentration when photometric readings are taken of unknown samples. Such curves, however, are only accurate for a particular set of reagents, or cuvettes (vials receiving the fluids) and for the specific instruments standardized at that particular time.

Thus, when new reagents and new cuvettes are used or the instrument is repaired, restandardization is necessary. Even when the same instruments are used, restandardization may be necessary due to changes in electronic components during the passing of time.

When direct read-out photometric systems are used, substantial effort is required to calibrate and adjust the instrument and to enter appropriate sealing factors required to obtain readings of certain quantities. Over time, the same readjustments and recalibrations to compensate for changes in electronic components, etc. are required to assure instrument accuracy. As a result, measurements of unknown samples are time consuming and subject to inaccuracies caused by operator error.

Other known methods of determining the chemical concentration of a substance in a biological fluid include electrolysis, resistance measurement, capacitance detection, and others. However, these methods often require calibration times that in some instances exceed the actual test time, are not as accurate, and are not operated as easily as photometric analysis.

SUMMARY OF THE INVENTION

The photometric system of this invention overcomes the disadvantages known to the prior art to accurately determine the amounts of selected chemical substances in biological fluids by comparing time-rate reactions.

A fluid having a known value of a chemical of interest is placed in a cuvette. A selected reagent is then added to the fluid to start a rate reaction. The cuvette is deposited in a receptacle and interposed between a light source of selected wave length and a phototube. The phototube provides a current output representing a change in the transmissibility of the fluid resulting from the rate reaction. The current from the phototube is applied to a logarithmic amplifier to provide a voltage proportional to the optical density of the fluid, as scaled by a calibrating amplifier. As the rate reaction proceeds, the voltage from the calibrating amplifier increases. An operator actuated switch is depressed to initiate a calibration mode which causes a timing circuit to measure the time it takes for the voltage from the calibrating amplifier to increase from a base-line level to a pre-set value. This time, referred to as the calibration time, is counted and stored for subsequent use.

A biological fluid sample containing an unknown amount of the chemical substance of interest is placed into a cuvette equal in quantity to that of the standard. An equal amount of reagent is then added to start a rate reaction. The cuvette containing the fluid is then placed in the same receptacle and a test mode is initiated. Light from the light source is passed through the fluid, and a current proportional to the transmissibility of the fluid is provided to the logarithmic amplifier. The voltage from the logarithmic amplifier increases as the rate reaction of the sample proceeds and is scaled by the calibrating amplifier. The increasing voltage from the logarithmic amplifier is measured from a base-line level for a time period equal to the calibration time. An analog to digital converter is employed to convert the voltage into a binary signal which is applied to a digital display. The display is operative at the end of the calibration time period and the digital value representing the voltage change at that time also represents the value of the unknown sample. Since the voltage change employed to establish the calibration time period and the voltage change to determine the value of the unknown sample are each measured from a base-line, and since the voltage change for the unknown is measured during a period equal to the calibration time, zero adjustments of the equipment are unnecessary.

It is a feature of the present invention to provide an improved photometric system for the analysis of a chemical substance in biological fluids, which reduces the need for operator adjustment.

Another feature of the invention is to provide such a photometric system which employs fixed time rate reaction of standard solutions to provide an accurate calibration reference time for the analysis of an unknown sample.

A further feature of the invention is to provide a photometric system which measures the voltage increases representing the ongoing rate reaction from a base-line level during the calibration time period.

Another feature of the invention is to provide such a photometric system which, by the use of similar testing and calibration circuits along with sequential measurements of the fluid standard and the unknown fluid, provide for an accurate measurement of the unknown with respect to the standard.

Yet another feature of the invention is to provide a photometric technique for enabling the analysis of unknown substances in biological fluids which can be practiced by unskilled personnel.

DESCRIPTION OF THE PREFERRED EMBODIMENT

Figure 1:
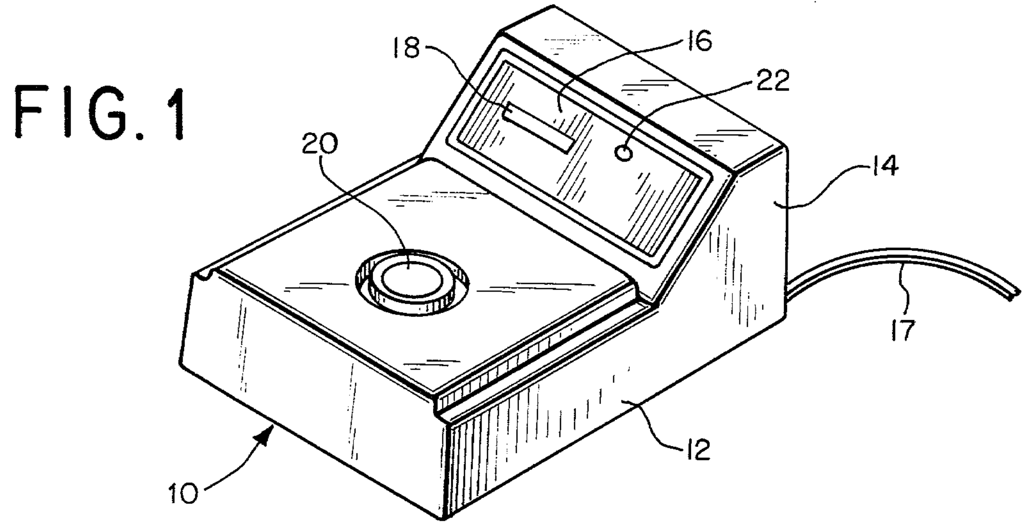
FIG. 1 is a perspective view depicting the photometric system of the present invention.

Referring to FIG. 1, the photometric system includes a housing 10 having a base portion 12 and an end portion 14 with a display panel 16 positioned therein. The system is provided power by cord 17. The display provides a digital readout 18 representing the value of a selected chemical substance in a container of biological fluid deposited in receptacle 20. The system 10 also includes a push button 22 for initiating the calibration mode of the system, and indicator lights (not shown) signalling operation of the system in the calibrate or test mode. The receptacle 20 is constructed to receive a cuvette or similar transparent vial for insertion into a light path defined by a radiant source and a photodetector circuit, as will be subsequently described. Although the system 10 has broad and general use in most aspects of medical diagnostic instrumentation, the system is particularly useful in measuring chemical substances such as glucose, blood urea, nitrogen, bilirubin and creatine in biological fluids such as whole blood, blood serum or blood plasma, and urine.

Figure 2:
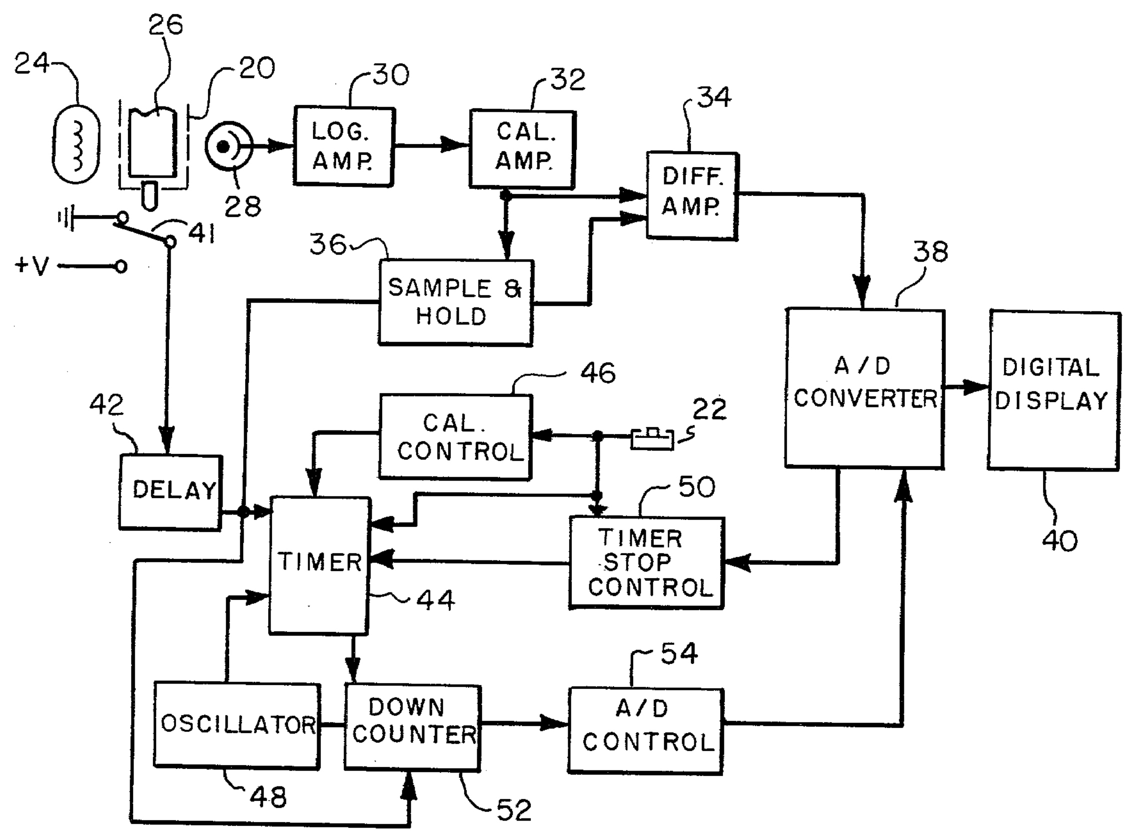
FIG. 2 is a functional block diagram of the circuits forming the system of of FIG. 1.

Referring to FIG. 2, the interconnection of the functional components of the system will now be described. The biological solution to be used with the photometric system is contained within a transparent cuvette or vial deposited in receptacle 20, thereby placing the substance between light source 24 and phototube 28. Light from source 24 is directed through suitable openings in the base (not shown) and passes through the cuvette 26 and its contents to the phototube 28. The output from the phototube 28 is a current proportional to the amount of light passing through the cuvette 26 and its contents which falls upon the phototube 28. Among other things, the amount of light which falls upon the phototube 28 is dependent upon the transparency of the fluid in the cuvette.

The current from the phototube 28 is provided to a logarithmic amplifier 30 which provides a transfer function to convert the current into a voltage proportional to the logarithm of the current. The voltage output from the logarithmic amplifier 30 is provided to a calibrating amplifier 32. The gain of amplifier 32 may be set to provide a known voltage (as 0.2 v) for a known concentration of the chemical substance (as 200 mg/dl). The selected concentration is, for example, expressed in milligrams per deciliter. The gain of amplifier 32 is adjustable and the output is provided to the input of a differential amplifier 34 and a sample and hold amplifier 36. The output from the differential amplifier 34 is provided to an analog to digital converter 38 which converts the analog signal into a digital signal for the operation of display 40. When energized at a particular time, as will be discussed in detail below, digital display 40 provides a digital representation of the voltage at the output of amplifier 34.

Predetermined quantities of a calibration standard (i.e., a fluid having a predetermined known amount of chemical substance per unit of the liquid, as 200 mg/dl) and a reagent, as a selected enzyme, are added to the solution to initiate a time rate reaction. The cuvette is then placed into the receptacle 20, at which time contacts of a normally open switch 41 (FIG. 2), lying along the floor of receptacle 20, are closed to provide power to a delay circuit 42. The delay circuit 42 establishes a predetermined time delay giving the operator sufficient time to depress calibrate button 22, initiating the calibration mode of the system. At the conclusion of the predetermined time delay, a pulse is provided to sample and hold circuit 36. When the sample and hold circuit 36 receives the pulse, the voltage at the output of the sample and hold circuit is provided to differential amplifier 34 until cuvette 26 is removed from the receptacle 20, as detected by the opening of the contacts of switch 41. The output of the differential amplifier 34 is a voltage which represents the algebraic difference between the inputs of the differential amplifier 34. The voltage referred to as a base-line voltage, is thus established at the output of sample and hold circuit 36 from which the voltage change at the output of calibrating amplifier 32 can be measured.

Immediately after the calibration standard along with the added reagent has been inserted into the receptacle 20, and after the predetermined time delay has passed, calibration of the system is initiated. Specifically, push button 22 is depressed to initiate calibrate control circuit 46. To assure that proper calibration occurs, the calibrate button must be depressed prior to the time at which a pulse from delay 42 occurs otherwise the fixed time period, to be subsequently measured, will be inaccurate.

When the push button 22 has been depressed, and an output pulse is provided by delay 42, a timing circuit 44, driven by oscillator 48, is initiated. The timer continues to run until the output of the analog to digital converter 38 reaches a predetermined value representing a specific amount of voltage change from the base-line voltage at the output of sample and hold circuit 36. A signal from the analog-digital converter 38 is provided to timer stop control 50 which, in turn, stops timing circuit 44. The period of time required for the voltage from the calibrating amplifier 32 to increase from the base-line level to the preset level is stored in level 44. This time is referred to as the calibration time and is retained in storage until the system is again operated in the calibration mode. After the analog to digital converter 38 reaches the predetermined level, the analog to digital converter 38 is stopped at that value indicating to an operator that the calibration is complete. The cuvette containing the calibrated standard may then be removed and the system is ready to receive a cuvette containing a biological fluid containing the chemical substance of unknown amount.

An identical quantity of biological fluid containing the unknown amount of chemical substance of interest is then placed into a cuvette and a reagent is added to initiate the rate reaction. The cuvette is placed into the receptacle 20 and switch 41 closes, and after the time delay provided by delay 42 is complete, an output pulse is simultaneously provided to sample and hold circuit 36 and down counter 52. Thus, at the completion of the time delay, the signal in the sample and hold circuit 36 is stored and provided, as an input, to differential amplifier 34. The voltage from the sample and hold circuit 36 represents a base-line from which the voltage increase from calibration amplifier 32 is measured.

The pulse from the delay circuit 44 which was received earlier by down counter 52 causes the down counter to store the calibration time held by timer 44 and to start counting down to zero, as clocked by oscillator 48. Since the rate reaction in the biological fluid containing the unknown amount of chemical substance to be measured is continuing, the voltage from the base-line level at the output of differential amplifier 34 increases and continues to increase until the down counter 52 reaches zero, at which time an output pulse from the A to D control circuit 54 causes the analog to digital converter 38 to stop. Analog to digital converter 38 makes the conversion from the analog signal to a digital signal and retains the value present at the time the down counter 54 reaches zero. This value is displayed as a direct measurement of the concentration of the chemical substance of interest, with respect to the standard solution.

Figure 3A:
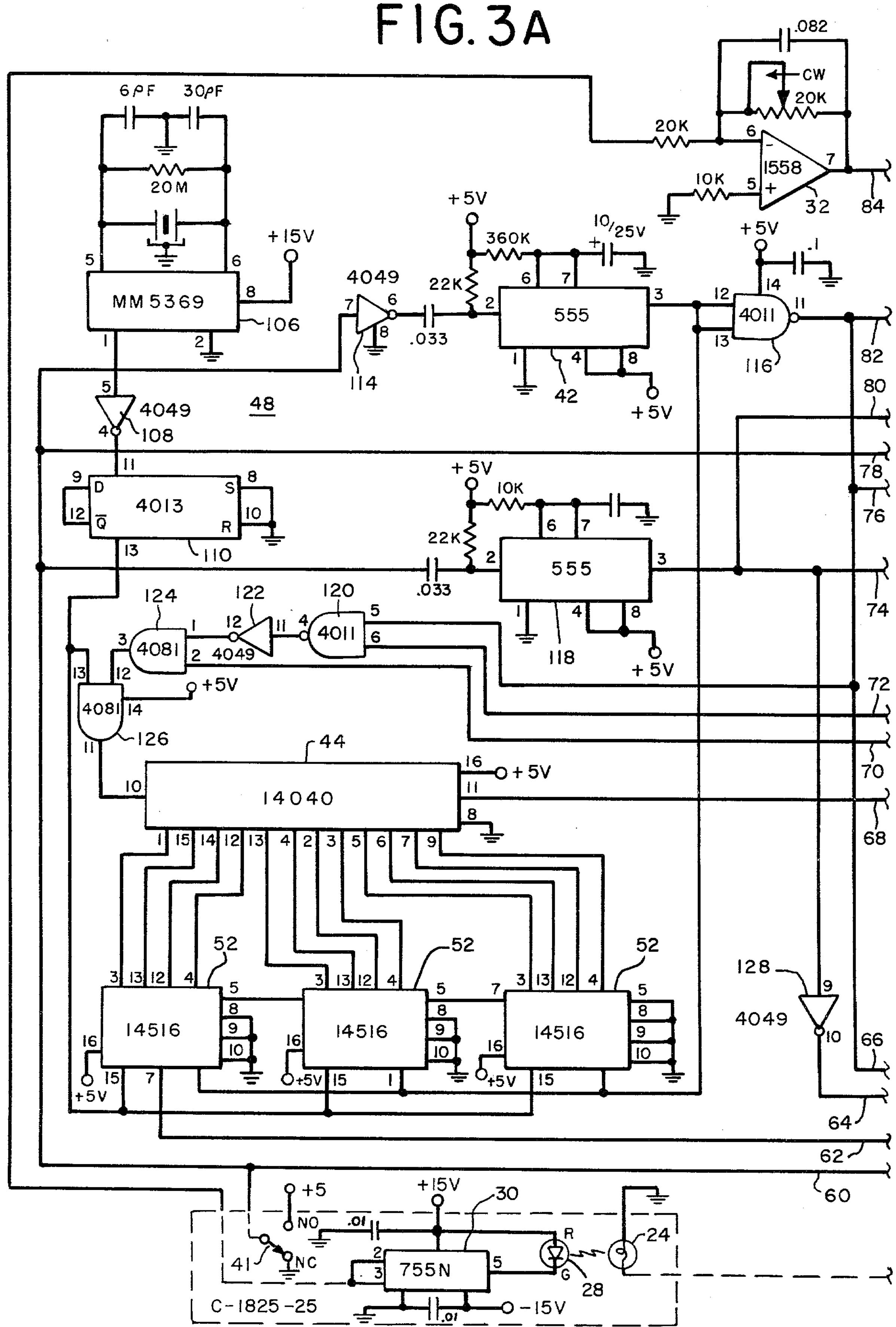
FIG. 3A, FIG. 3B, and FIG. 3C together form a detailed schematic diagram showing a particular connection of elements of the circuit in FIG. 2.
Figure 3B:
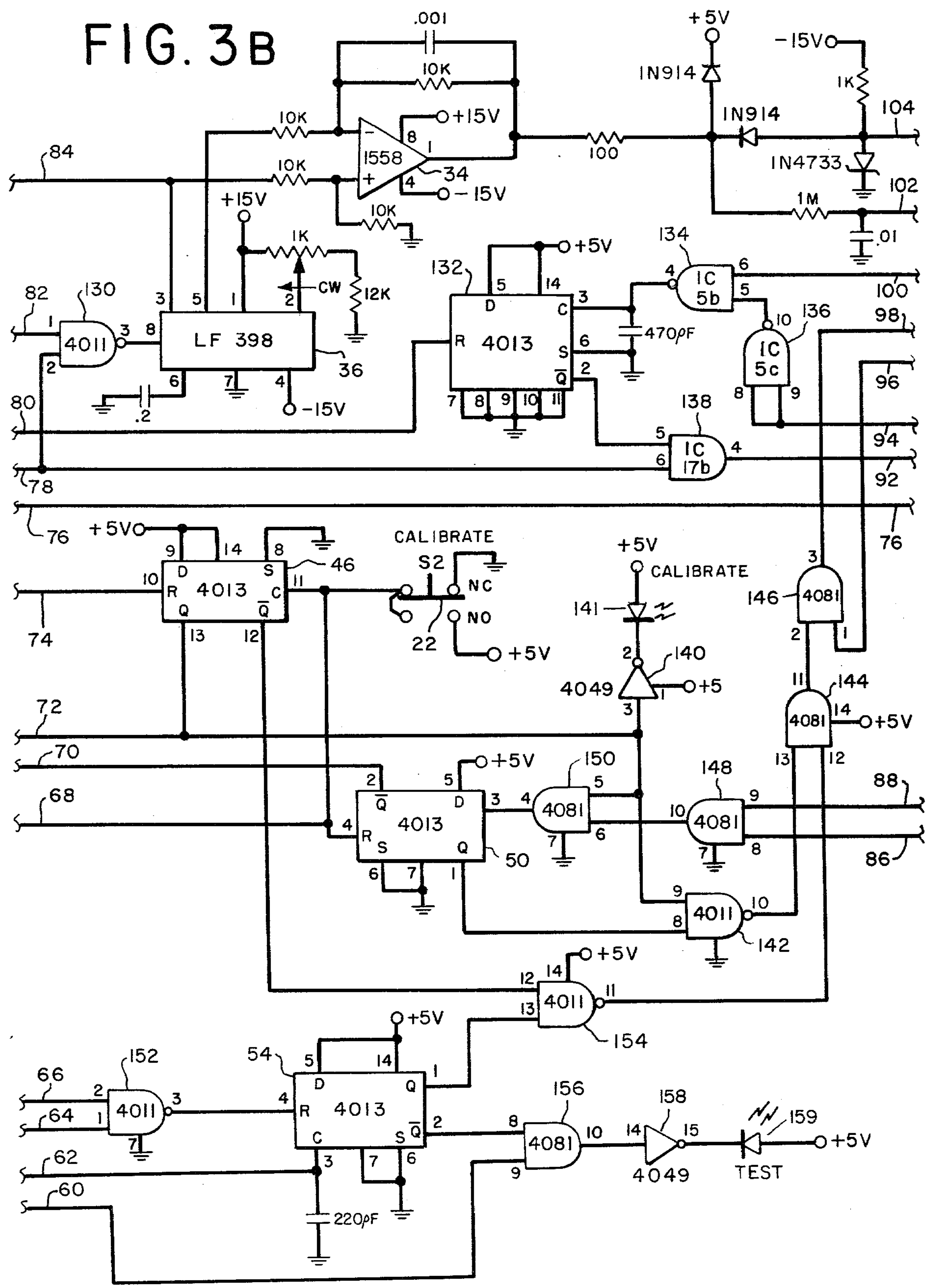
Figure 3C:
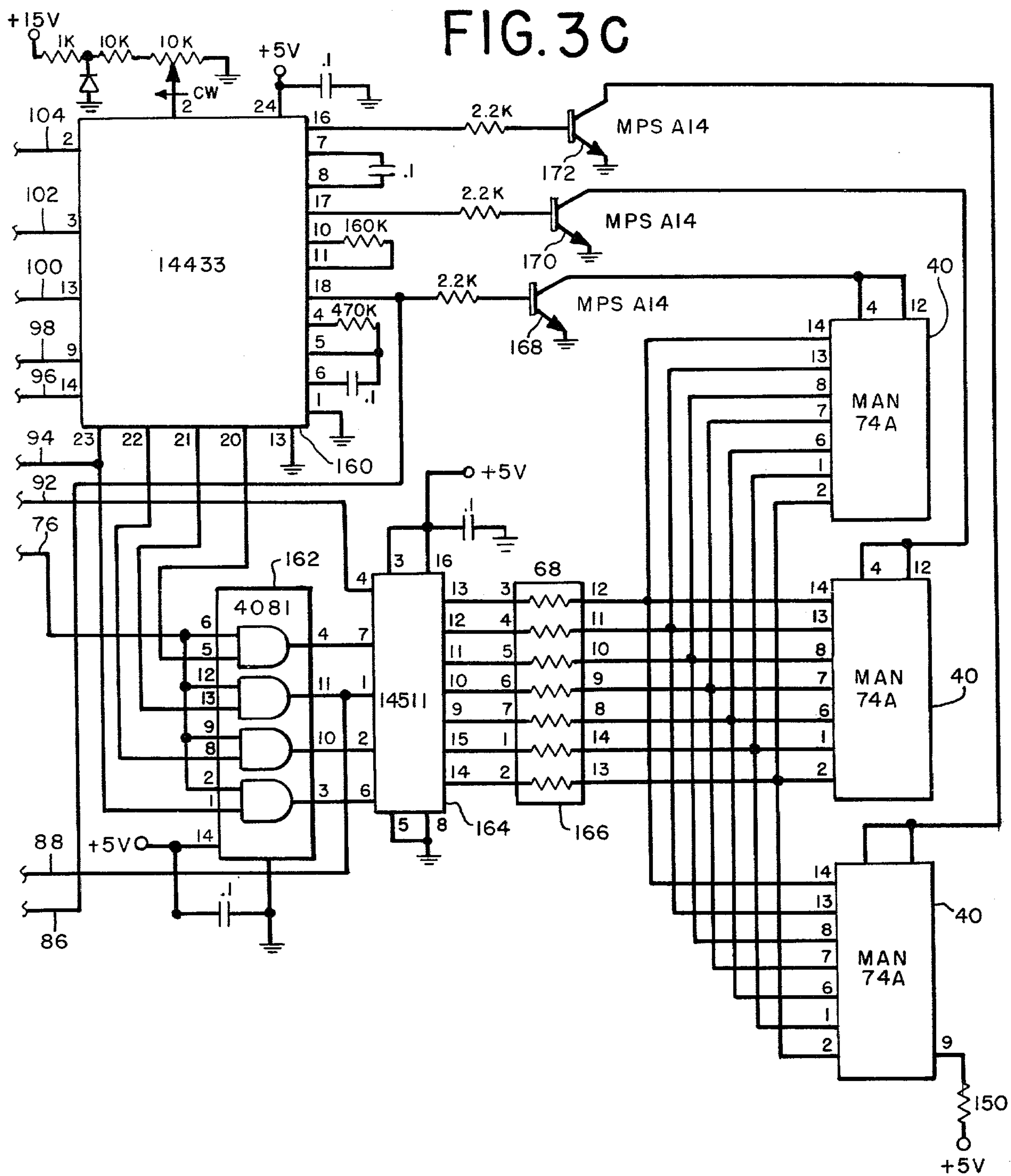

Referring now to FIG. 3A, FIG. 3B, and FIG. 3C, specific components and interconnections are shown to accomplish the previously described measurement of the amount of unknown samples. The particular interconnections and values of the various components are shown in detail. The operation of the circuits will therefore be apparent upon reviewing the drawing. The drawing will be described in only as much detail as is necessary to understand the functional cooperation of the circuits for a specific application, it being understood that all values for resistance are in ohms, for capacitance in microfarads, and all other elements identified by their numerical designations well known in the art unless otherwise shown.

By way of example, the illustrated circuits are coupled and set to measure the concentration of glucose in unknown samples using a 200 milligram per deciliter (mg/dl) concentration on the standard solution. In order to prepare the standard solution 5 milliliters (ml) of a working buffer are dispensed into a cuvette to which is added 20 microliters (ul) of of the standard solution. 0.1 ml enzyme reagent is then added and swirled to initiate the time rate reaction. The cuvette with the mixture should then be inserted into receptacle 20 within 10 seconds.

Turning first to FIG. 3A, a lamp 24 or other radiant energy source directs light through an appropriate filter (not shown) and through the cuvette (shown in FIG. 2) to the photodiode 28. The current from photodiode 28 is coupled to logarithmic amplifier 30 which provides an increasing voltage changing at a constant rate representing the change in optical density of the chemical. This voltage is coupled as the input to calibrating amplifier 32 to provide an output at 84. In this example the amplifier 32 is set to provide a voltage of 0.2 volts for a glucose concentration of 200 mg/dl. The output of amplifier 32 is coupled as an input to sample and hold 36 and as one input to differential amplifier 34.

The oscillator 48 (FIG. 2) includes serially coupled elements 106, 108 and 110 to provide a clock signal as one input to AND-gate 126 and the down counter 52.

Switch 41, which is normally coupled to ground, is closed to contact a +5 v source when a cuvette is inserted into the receptacle 20. The signal from switch 41 is coupled to one input of AND-gate 156 via line 60, to the input of integrated circuit 118, to one input to NAND-gate 120 and one input to AND-gate 138 via line 78 and to inverter 114. The output of inverter 114 is coupled to integrated circuit 42 which is a delay timer and provides an output pulse 4 sec after switch 41 is closed. The output from the delay 42 is coupled to the inputs of NAND-gate 116 and and an input to the down counters 52. The output from NAND-gate 116 is connected via line 82 to NAND gate 130, via line 76 to the circuit 162 in the analog to digital converter 38, to one input of NAND-gate 120 and to one input of NAND-gate 152 via line 66.

The output of integrated circuit 118 is coupled to the reset input of integrated circuit 132 via line 80, to the reset input of calibration control 46 and through inverter 128 to the other input of NAND-gate 152 via line 64.

The output of NAND-gate 120 is coupled through inverter 122 to one input of AND-gate 124. The output from AND-gate 124 is coupled to the other input of AND-gate 126. When AND-gate 124 provides a high output, the oscillator 48 clocks the timer 44 to store the time for as long as the high signal from 124 remains. The timer then provides its output to the down counters 52 for storage of the reference calibration time as previously described and an output to the reset of timer stop control 50 via line 68.

Turning next to FIG. 3B, the output from NAND-gate 130 is coupled to sample and hold circuit 36 to cause storage of the voltage signal on line 84 in response to the pulse provided by delay circuit 42, 4 sec after closure of switch 41. The stored voltage is provided at an output of sample and hold circuit 36 and coupled to the other input of differential amplifier 34. The output from amplifier 34 is coupled to circuit 160 in analog to digital converter 38 via line 102 and 104. The signal provided at the output of amplifier 34 is an increasing voltage starting at a base-line established by the stored voltage output provided to the negative input of differential amplifier 34.

An output from integrated circuit 132 is coupled to the other input to AND-gate 138, the output of which is coupled as an input to decoder circuit 164 in analog to digital converter 38. NAND-gate 136 has its output coupled to one input of NAND-gate 134 having its output coupled to the clear input of integrated circuit 132.

Calibration push button 22 is coupled to provide a signal to calibration control circuit 46, and to the reset of timer stop control 50. The output from the Q output of calibration control 46 is coupled to the other input to NAND-gate 120 via line 72, to one input of AND-gate 150 and NAND-gate 142, and through inverter 140 to the cathode of a light emitting diode 141 forming the calibrate indicator which is energized to show that the system is in the calibration mode when a low signal appears at the output of 140. The Q output of calibration control 46 is coupled to one input of NAND-gate 154.

The NAND-gate 152 provides an output signal to the reset pin of analog to digital control 54. The Q output of control 54 is coupled to the other input to NAND-gate 154 having its output connected to one input of AND-gate 144. The Q output of control 54 is coupled as the other input to AND-gate 156. The output of AND-gate 156 is then coupled through inverter 158 to the cathode of a light emitting diode coupled 159 to cause light emission when the output of inverter 158 goes low. The diode 159 is energized during the test mode and remains on until the down counters 52 have reached zero count indicating the test is complete.

The output from pin Q of calibrate control 50 is coupled to the other input of NAND-gate 142. The output of NAND-gate 142 is, in turn, coupled to the other input of AND-gate 144 having its output connected to one input of AND-gate 146. The output of AND-gate 146 is then coupled to circuit 160 through line 98 to cause the analog to digital converter to stop or convert depending on the signal from AND-gate 146. The output of AND-gate 150 is coupled to the clear input of timer stop control 50.

Turning now to FIG. 3C, outputs from the circuit 160 of the analog to digital converter are coupled through individual transistors 168, 170 and 172 to drive digital display 40. In addition, the outputs from circuits 162, 164 and 166 are coupled to decode the digital values in display elements 40. Additional outputs from circuit 162 and circuit 160 of the analog to digital converter are coupled as the inputs to AND-gate 148 via lines 86 and 88. Further outputs from circuit 160 are also coupled as the inputs of NAND-gate 136 via line 94, to NAND-gate 134 via line 100, and to AND-gate 146 via line 96.

When this system is operated in the calibration mode the calibrate button must be pushed within 4 seconds after inserting the cuvette into the receptacle 20. If this is not done, the base-line level will be entered by sample and hold circuit 36, but the beginning of the timing period will not coincide with the beginning of voltage change from the base-line level. As a result, the fixed time calibration for the specific concentration of standard will not be accurately recorded and subsequent tests will be made based on erroneously measured rate of change.

If the calibrate button is pushed within 4 seconds after insertion of the cuvette, the timer and calibration control circuits are reset and the sample and hold amplifier holds the signal voltage level present at 4 seconds until the cuvette is removed from the receptacle 20. This voltage represents the base-line for the reaction and is subtracted from the voltage at line 84 in the differential amplifier as the reaction proceeds. When the timer is reset it starts counting pulses from the oscillator 48 until the analog to digital display 40 reads 200 which is a measure of the voltage change for the pre-established concentration for the standard solution. When the analog to digital converter reads 200 it sets calibration control 50 to a high level and thereby turns the timer off and stops the output of the analog to digital converter so that the 200 is displayed until the cuvette is removed. At this time, the timer contains the fixed time required for the standard solutions to change from the base-line to a preset value of 200.

Subsequently, in order to run a test operation, 20 $\mu$l of an unknown sample are dispensed in 5.0 ml of a working buffer in the cuvette. After allowing for any settling time (30 seconds for whole blood), 0.1 ml of reagent is added and swirled. The cuvette is then inserted into the receptacle 20 to depress switch 41, within 10 seconds.

The operation of the system at this time is similar to that during the first 4 seconds when the standard was inserted. However, after 4 seconds if the calibrate button is not pushed, the time stored in the timer 44 is transferred to the down counters 52 and the analog to digital converter 38 is permitted to convert the differential voltage until the down counters reach zero. At this time a pulse from one of the counters sets the analog to digital control circuit to stop the analog to digital converter and display the reading at that instant. The test lamp which is located on display panel 16 will then go out indicating that the displayed number is a measure of the amount of the chemical substance contained in the sample solution.

As is apparent from the above description, since the time rate of change of the standard is being used to establish a fixed time period as the calibration time required for a voltage to change from a base-line level to a fixed value, and since the voltage change of an unknown is measured during the same time period, there is no need for zeroing or gain calibration or other operator interference. This device can be calibrated for testing each time it is used by merely inserting a standard solution, and pushing the calibrate button. Subsequent consecutive tests of different samples will then give a concentration value for the unknown without further adjustments.

While the system and technique have been described with reference to the particular circuits of FIG. 3, it is apparent that other configurations are possible in accordance with the present teachings.

We claim:

1. A system for measuring an unknown amount of a selected chemical substance in a biological first fluid comprising:

means for measuring the optical density of a fluid during a rate reaction;

means for providing a voltage proportional to the optical density of a fluid during its rate reaction;

means responsive to said proportional voltage for providing a difference voltage;

means for measuring a period of time equal to the time required for the difference voltage of a second fluid to increase from one level to a selected higher level during a rate reaction; and means for displaying a difference voltage representative of a change in the optical density of said first fluid at the conclusion of the period of time required for the difference voltage of the second fluid to increase from one level to a selected higher level.

2. The system of claim 1 wherein said means for measuring the optical density of a fluid during a rate reaction comprises:

a source of radiant energy;

means for detecting the radiant energy and providing a current output proportioned to optical density; and means for receiving and positioning a fluid in the energy path between the source and detecting means.

3. The system of claim 1 wherein said means for providing a difference voltage comprises:

means for sampling and holding the voltage at a given time during the rate reaction to form a base-line voltage;

means for subtracting the base-line voltage from the voltage as the reaction continues to form a difference voltage.

4. The system of claim 2 further comprising:

means responsive to the receiving means for indicating the presence of a fluid;

means responsive to said indicating means and coupled to said means for providing a difference voltage for enabling the provision of a difference voltage a predetermined time after an indication of fluid presence in the receiving means.

5. The system of claim 4 wherein said means for measuring a period of time comprises:
a means for providing a calibrate signal;
timer means responsive to the calibrate signal and the enabling means for initiating and storing a timing period; and
means responsive to the display means for terminating the timing period when the difference voltage measured for one fluid reaches a predetermined value.

6. The system of claim 3 further comprising:
means for receiving and positioning a fluid in the energy path between the source and the detecting means;
means responsive to the receiving means for indicating the presence of a fluid; and
delay means responsive to the indicating means and coupled to said sample and hold means for preventing the formation of said base-line for a predetermined period.

7. The system of claim 1 wherein said means for measuring a period of time comprises:
means for providing a calibrate signal;
timer means responsive to said delay means and calibrate signal for initiating and storing a timing period; and
means responsive to said difference voltage for terminating the timing period when the difference voltage measured for one fluid reaches a predetermined value.

8. The system of claim 7 further comprising:
counter means coupled to said timer means for storing a count representing the stored time period and responsive to the delay means for initiating a down count; and
control means responsive to the counter means reaching a zero count for causing the display means to display the difference voltage.

9. The system of claim 8 further including an oscillator means coupled to clock the timer means, and counter means for controlling the rate of timing and counting.

10. A system for measuring chemical substances in biological fluids comprising:
means for providing a source of radiant energy;
means for detecting radiation from said source and providing a voltage output;
means for receiving and positioning a sample of fluid, in which a rate-reaction has been initiated, in the energy path between the source and detecting means;
means operable in a calibrate mode to measure a time period during which the voltage changes by a predetermined amount when a known concentration sample is positioned in the receiving means, and operable in a test mode for measuring the voltage change during a time equal to the previously measured time period when an unknown sample is positioned in the receiving means; and
means for displaying the measured voltage change during the test mode.

11. The system of claim 10, wherein said means for detecting radiation and providing a voltage output include:
means for detecting the radiation and converting the detected radiation to a voltage signal;
means for sampling and holding the voltage signal at a given time during the rate-reaction to form a base-line voltage signal; and
means for subtracting the base-line voltage signal from the voltage signal as the reaction continues to form a difference voltage signal as the output voltage.

12. A method of determining the amount of a selected chemical substance in a first biological fluid carrying an unknown amount of the selected chemical by comparing a rate reaction of the biological fluid to a rate reaction of a second biological fluid carrying a known amount of the selected chemical substance, comprising:
subjecting the second fluid to a light source;
providing a first voltage proportional to light passing through said second fluid as the rate reaction continues;
measuring the time required for the first voltage to increase from one level to a selected higher level;
subjecting the first fluid to the light source;
providing a second voltage proportional to the light passing through said first fluid;
measuring the second voltage for a period of time equal to the time required for the first voltage to increase from said one level to said selected higher level;
displaying the measured second voltage at the conclusion of the period of time to provide an indication of the amount of selected chemical substance in said first fluid.

13. A method of measuring an unknown amount of a selected chemical substance in a biological fluid, comprising:
selecting a fluid carrying a known amount of the selected chemical substance;
initiating a rate-reaction in the fluid carrying the known amount of the selected chemical substance;
exposing the fluid to a light source while the rate-reaction continues;
measuring the optical density of the fluid carrying the known amount of the selected chemical substance while the rate-reaction continues;
providing a first voltage proportioned to the optical density of the fluid carrying the known amount of the selected chemical substance as the rate-reaction continues;
measuring and storing the amount of time required for the voltage to increase from a first level to a second level to provide a calibration reference time;
initiating a rate-reaction in the fluid carrying the unknown amount of the selected chemical substance;
exposing the fluid carrying the unknown amount of the selected chemical substance to the light source while the rate-reaction continues;
measuring the optical density of the fluid carrying the unknown amount of the selected chemical substance while the rate-reaction continues;
providing a second voltage proportional to the optical density of the fluid carrying the unknown amount of the selected chemical substance as the rate-reaction continues;
measuring the second voltage for a period of time equal to the calibration reference time; and
measuring the second voltage at the end of the calibration reference time to provide an indication of the amount of selected chemical substance in the biological fluid.

* * * * *